United States Patent
Grover et al.

(10) Patent No.: US 10,682,068 B2
(45) Date of Patent: Jun. 16, 2020

(54) SYSTEM AND METHOD FOR HIERARCHICAL REFERENCING FOR BIOPOTENTIAL MEASUREMENTS

(71) Applicant: CARNEGIE MELLON UNIVERSITY, Pittsburgh, PA (US)

(72) Inventors: Pulkit Grover, Pittsburgh, PA (US); Shawn Kelly, Pittsburgh, PA (US); Jeffrey Weldon, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 163 days.

(21) Appl. No.: 15/580,249

(22) PCT Filed: Jun. 27, 2016

(86) PCT No.: PCT/US2016/039539
§ 371 (c)(1),
(2) Date: Dec. 6, 2017

(87) PCT Pub. No.: WO2016/210407
PCT Pub. Date: Dec. 29, 2016

(65) Prior Publication Data
US 2018/0146878 A1   May 31, 2018

Related U.S. Application Data

(60) Provisional application No. 62/231,168, filed on Jun. 26, 2015.

(51) Int. Cl.
*A61B 5/0478* (2006.01)
*G16B 5/00* (2019.01)
*A61B 5/04* (2006.01)
*A61B 5/00* (2006.01)

(52) U.S. Cl.
CPC ........ *A61B 5/0478* (2013.01); *A61B 5/04012* (2013.01); *A61B 5/6802* (2013.01); *G16B 5/00* (2019.02); *A61B 2562/04* (2013.01)

(58) Field of Classification Search
CPC . A61B 5/0478; A61B 5/6802; A61B 5/04012; A61B 2562/0209; A61B 2562/04; G16B 5/00
See application file for complete search history.

(56) References Cited

U.S. PATENT DOCUMENTS

| | | |
|---|---|---|
| 6,374,202 B1 | 4/2002 | Robinson |
| 2002/0165674 A1 | 11/2002 | Bassett et al. |
| 2004/0170335 A1 | 9/2004 | Pearlman |
| 2008/0001735 A1 | 1/2008 | Tran |

(Continued)

OTHER PUBLICATIONS

International Search Report and Written Opinion for PCT/US2016/039539 dated Sep. 13, 2016.

*Primary Examiner* — Eric F Winakur
*Assistant Examiner* — Abid A Mustansir

(57) ABSTRACT

The present invention relates to a method of taking biopotential measurements, with the ability to perform in high-density sensing applications. The invention is a hierarchical referencing method for the electrodes in the biopotential measurement system that is able to recover potential at each location with respect to a global reference with smaller requirements on ADC resolution, and thus with lower power and area requirements as compared to current systems.

11 Claims, 5 Drawing Sheets

(56) References Cited

U.S. PATENT DOCUMENTS

| | | | | |
|---|---|---|---|---|
| 2008/0312523 A1* | 12/2008 | Dunseath | ............ | A61B 5/04004 600/383 |
| 2011/0015503 A1* | 1/2011 | Joffe | .................. | A61B 5/04004 600/301 |
| 2011/0257937 A1* | 10/2011 | Lee | .................... | A61B 5/04085 702/189 |

* cited by examiner

SYSTEM AND METHOD FOR HIERARCHICAL REFERENCING FOR BIOPOTENTIAL MEASUREMENTS

RELATED APPLICATIONS

This application is a national phase filing claiming the benefit of and priority to International Application No. PCT/US2016/039539 entitled "System and Method for Hierarchical Referencing for Biopotential Measurements" filed Jun. 27, 2016, which claims the benefit of U.S. Provisional Patent Application Ser No. 62/231,168, filed Jun. 26, 2015. All of the above are hereby incorporated by reference in their entirety.

BACKGROUND OF THE INVENTION

High-density sensing of biopotentials is gaining increasing interest in bio-imaging applications as well as in other applications such as health monitoring and neuroprostheses. However, these devices are severely energy constrained because of the energy required to sense and communicate high-resolution signals, as well as limitations on energy dissipated near the tissue. The energy and area constraints are ultimately what limit the maximum density (and number) of these devices.

It has been observed that spatially dense biopotentials tend to also be highly correlated. This is for multiple reasons, such as:

Distance from the source of potentials, for example in Electroencephalography (EEG), where 1-1.5 cm separate the brain from the scalp, acts as a low-pass spatial filter to electromagnetic waves, thereby reducing the content of high-spatial-frequency signals, and introducing high spatial correlations.

The underlying biological sources of electromagnetic (EM) waves often travel along contiguous paths, and exist over non-negligible volumes, thereby introducing spatial correlations even at the source level.

Sources of noise are often other biopotential sources themselves that are again spatially correlated.

Electrodes themselves act as spatial low-pass filters by spatially averaging electric potential around them.

Even with the highly correlated data, high-density sensing is required to gather important information buried even in the "less significant" bits of each observation. Because of decay of high spatial frequencies, as illustrated in FIG. 1, these lower order bits are the ones carrying high-resolution information. Perhaps as an acknowledgement of this fact, many state-of-the-art systems record each electrode at a very high precision, for example 24-bit analog-to-digital converters (ADCs), with 256 or more sensors. Small differences between recordings of nearby sensors matter, likely because these differences capture events that generate small variations in potential either due to their shallow depth or small spatial extent.

There are two commonly used topologies for biopotential electrode referencing. In the first topology, shown in FIG. 2, all electrodes are referenced directly against a global reference (sometimes called "unipolar" or "direct global referencing"). The corresponding tree has one root node with all other nodes as its children. This topology requires that all electrode ADCs be of very high precision in order to detect the small informative differences between each electrode.

FIG. 3 shows the second topology, sometimes called "sequential bipolar referencing," where each electrode is referenced to an electrode prior to it in a chain of electrodes leading to a tree where each node has one child. There are two problems with this simplistic electrode-chain strategy. In many applications, especially those pertaining to source localization and imaging, algorithms commonly use signals referenced against a global reference where potential is recovered with respect to a single global reference. While it may seem that adding the differentially sensed potentials appropriately would yield signal with respect to the global reference, that is incorrect due to errors also adding up, and quantization noises and errors introduced by the circuit components (such as the amplifier and the ADC) of the electrodes also add as the signals are added resulting in large overall noise. Further, it is necessary to verify almost all electrodes for good contact, for if one electrode in the chain has poor contact, then the recordings of all ensuing electrodes will be unusable.

SUMMARY OF THE INVENTION

This invention is a referencing mechanism to exploit these high spatial correlations to reveal information in lower order bits of electrodes' recordings while still spending low power and area, thereby allowing increased electrode density. Our starting point is a simple observation: because nearby electrode recordings are highly correlated, by referencing electrodes against a nearby electrode, one can reduce the magnitude of signal being recorded and thereby use ADCs of smaller resolution. One might think that it is reasonable to construct a chain of electrodes, with the next electrode referencing its signal against the previous electrode. However, as we will see later, the electrode noise, contributed by thermal noise, quantization noise, and noise from other sources, adds up across electrodes in a fashion that can increase the noise variance linearly with the number of electrodes.

DETAILED DESCRIPTION OF THE INVENTION

Figure 1:
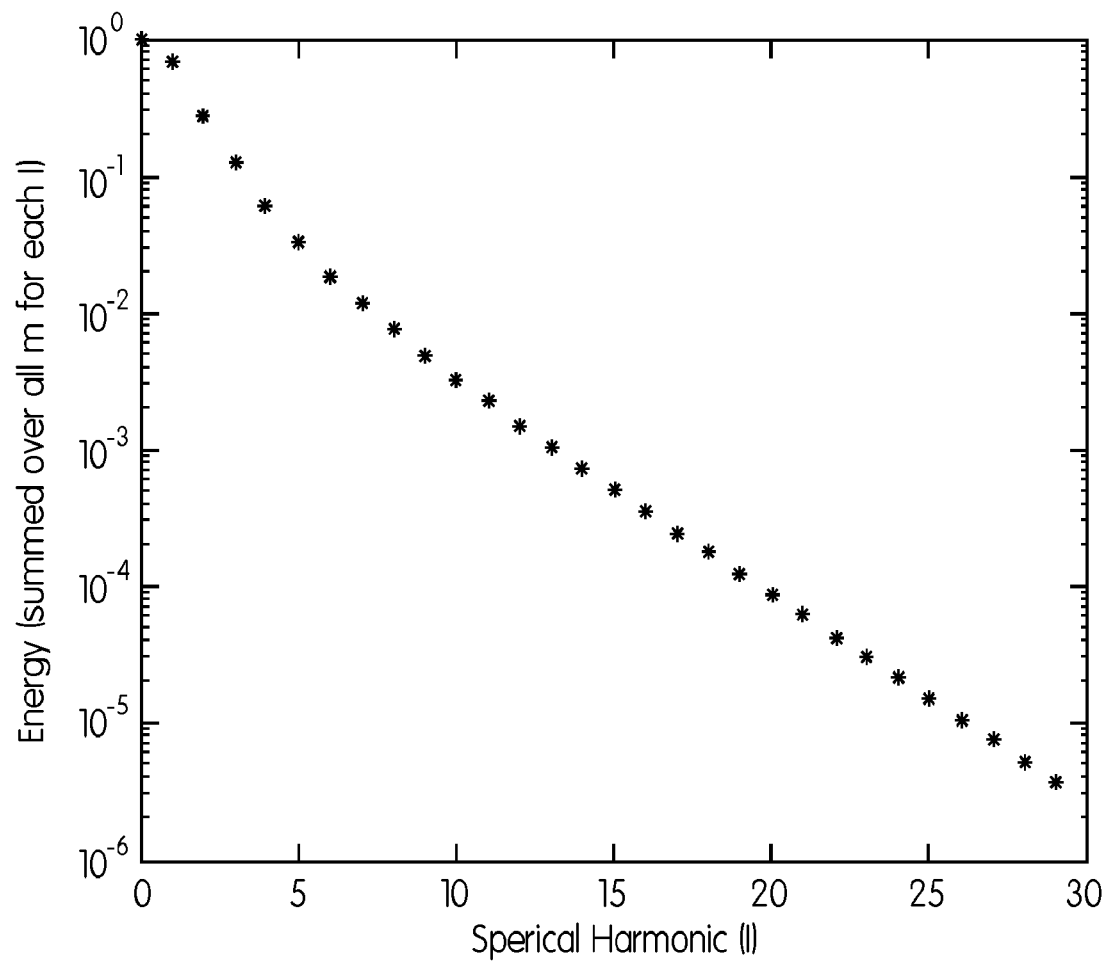
FIG. 1 shows the brain-surface to scalp transfer function (in spherical harmonics basis, increasing spherical harmonic index l corresponds to increasing spatial frequencies) using the 4-sphere model of the head with parameters $r_1=7.8$ cm, $r_2=7.9$ cm, $r_3=8.6$ cm, and $r_4=9.5$ cm, and conductivities of cerebrospinal fluid (CSF) layer 5 times, the skull $\frac{1}{80}$ times, and the scalp the same, as the conductivity of the brain.
Figure 2:
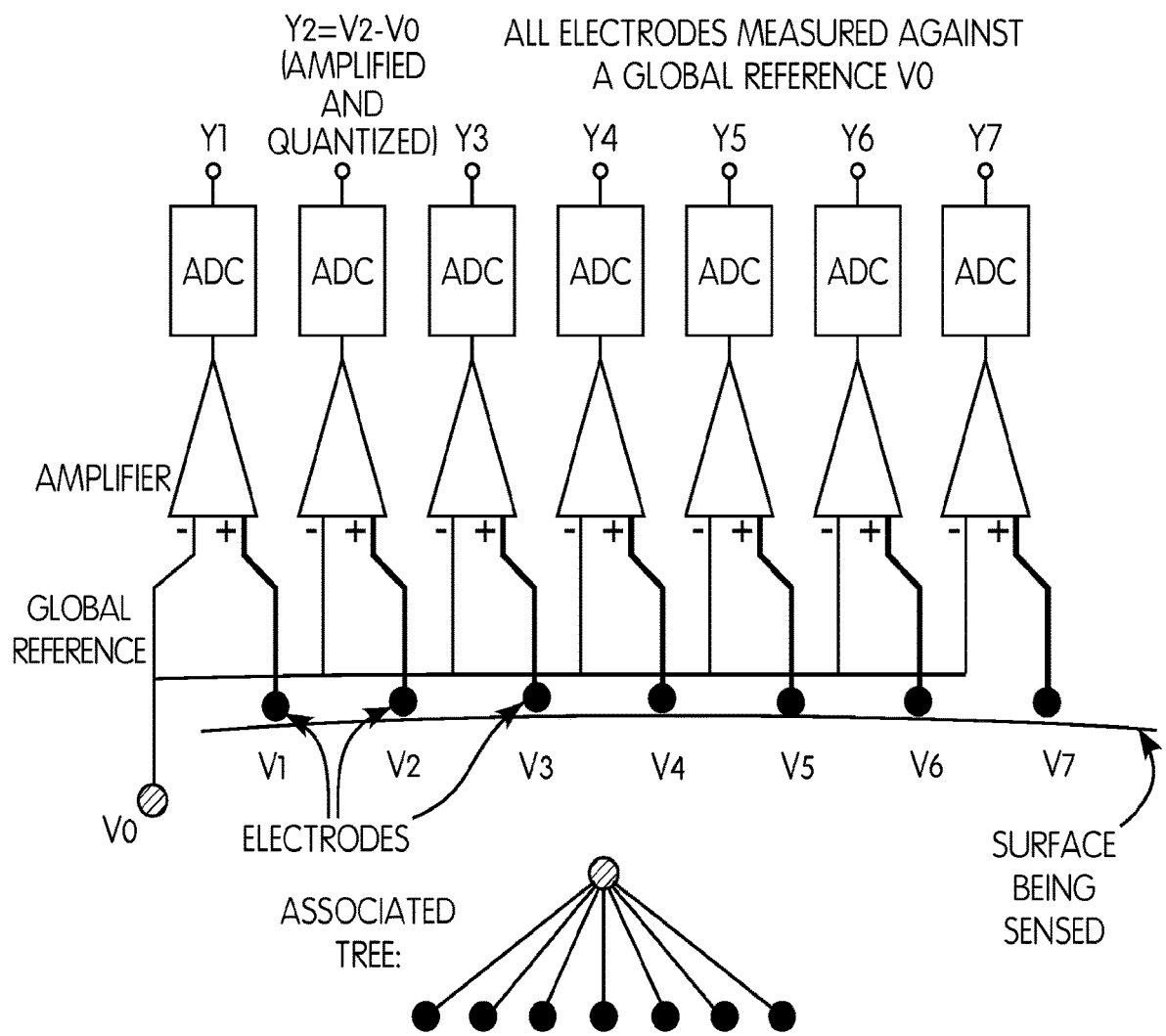
FIG. 2 illustrates 'direct global referencing', and the associated tree, where every electrode is referenced directly against a global electrode.
Figure 3:
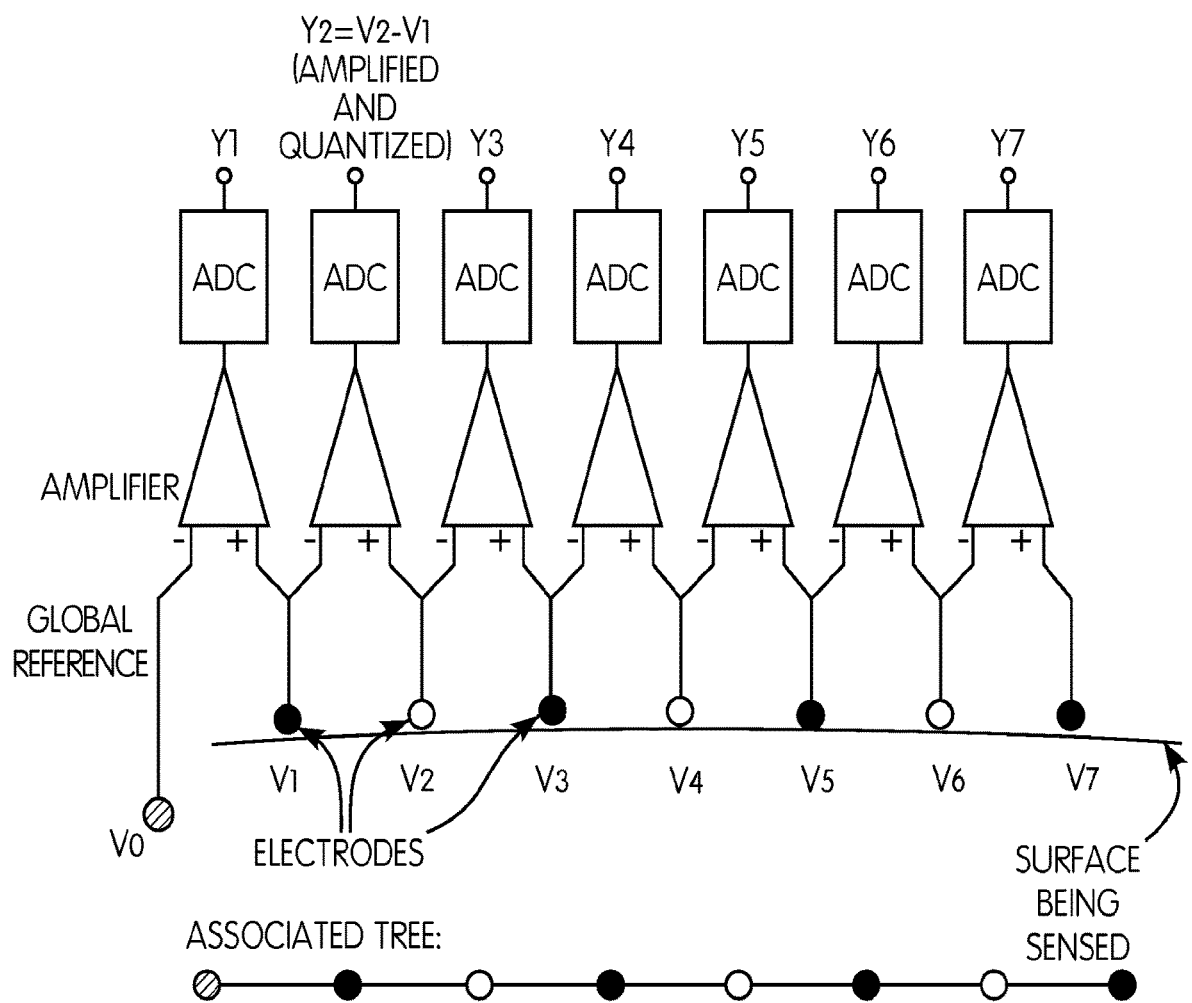
FIG. 3 presents sequential bipolar biopotential referencing and the associated tree.

For a variety of reasons, spatially dense biopotentials tend to be highly correlated. As an example, the spatial power-spectral-density of EEG as it passes through the CSF, the skull and the scalp is shown in FIG. 1. As such, there is important information buried in the least significant bits of each observation. Because of the decay of high spatial frequencies, as shown in FIG. 1, the least significant bits are precisely the bits in which high resolution information is buried. As a result, small difference between recordings of sensors in close physical proximity to each other capture events that generate small fields either due to their depth or spatial extent.

This invention is a hierarchical referencing strategy designed to exploit the high spatial correlations to reveal information at lower order bits of the recordings from electrodes. The strategy reduces noise accumulation significantly over sequential differential measurements while allowing low precision ADCs for the same overall noise as direct global referencing. In addition, there is a savings in both power and component expense, as less expensive analog to digital converters, having a smaller number of bits of resolution, can be used to detect the small differences between spatially close sensors.

Every referencing mechanism can be represented as an associated tree. Each electrode corresponds to one node in the tree. The global reference electrode is the root node; all nodes referenced directly against the global root node are nodes at level 1. All nodes referenced directly against level 1 nodes are level 2 nodes, and so on. In the tree, a node's parent is the node the corresponding node is referenced against. Because each node has exactly one parent, the graph of the topology of the nodes is a tree.

Figure 4:
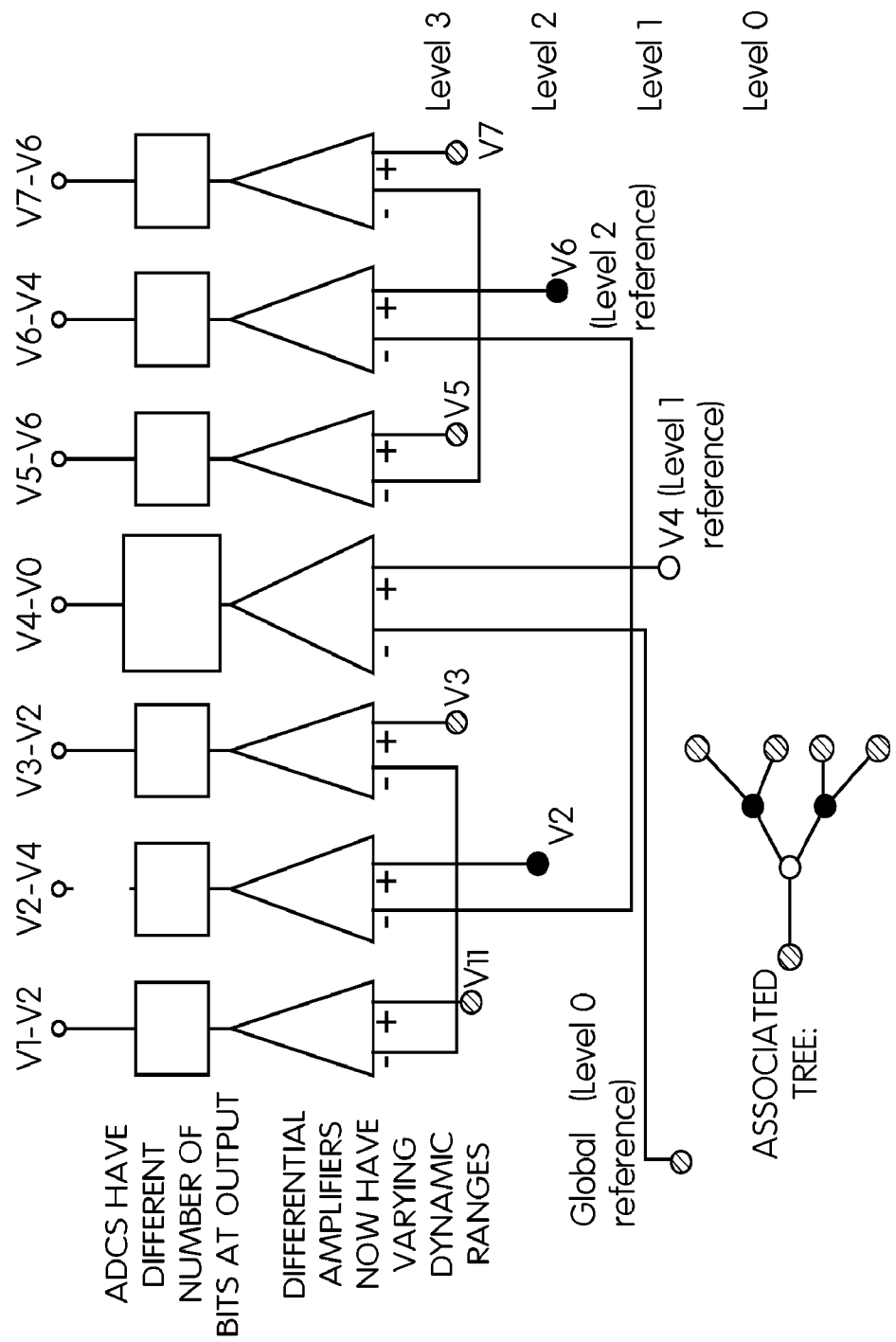
FIG. 4 shows the new hierarchical referencing strategy. For clarity, the differences of voltages being measured are indicated on the top.

The mechanism proposed in this invention is illustrated in FIG. 4. Instead of using sequential bipolar referencing, the electrodes are arranged in a tree pattern with a number of levels that can be optimized based on spatial correlations. For placement of electrodes along a grid, one can envision the grid as a hierarchical subdivision of squares. In case of placement of electrodes on a spherical surface, commonly used techniques are inherently recursive (e.g. icosahedron bisections used in EEG grids) and lend themselves naturally to hierarchical constructions of unequal but roughly constant degree per level.

To show the improvements of this invention over current methods, a comparison of this invention is first done with the sequential bipolar strategy. Input-referred noise variance for all electrodes is assumed to be the same regardless of strategy. To recover potential $V_i - V_0$ from measurements $Y_1 = V_1 - V_0 + Z_1, Y_2 = V_2 - V_1 + Z_2, \ldots, Y_i = V_i - V_i - 1 + Z_i$, one can simply add these potentials:

$$\sum_{j=1}^{i} Y_j = \sum_{j=1}^{i} (V_j - V_{j-1} + Z_j) = V_i - V_0 + \sum_{j=1}^{i} Z_j,$$

and thus noise variance increases linearly with the number of electrodes.

On the other hand, the hierarchical referencing strategy has a slower increase in noise. For instance, consider a tree where every node has D children. Then, to reach every node, one only requires to sum of $O(\log(n))$ terms, and the noise also grows only logarithmically.

Alternatively, in sequential bipolar referencing, one could allocate different levels of resolution to different electrodes, for e.g., by allocating increasing number of bits of ADCs as the electrode gets farther from the reference electrode. To compare with hierarchical referencing, let us assume that the noise in the worst case is $\log(n)$ as well. In that case, one could use $$\sigma_{zi}^2 = \sigma_{z0}^2 / i,$$

because $$\sum_{i=1}^{n} \frac{1}{i} \sim \log(n).$$

However, this requires at least half the electrodes to have noise variance $$\sigma_{zi}^2 \leq 2\sigma_{z0}^2 / n,$$

which reduces to zero as n increases. This noise variance can be kept constant in the hierarchical strategy for $\log(n)$ increase in overall noise).

The hierarchical strategy also makes it easier to ensure good contact. As long as the fewer electrodes in the higher layers have good contact, the larger number of electrodes in the lower layers will be sensed accurately. Having poor contact in the lowest layer hurts only the particular electrode with poor contact because there are no further electrodes that reference against the lowest layer.

We also note that the hierarchical strategy's tree structure provides an additional benefit: it reduces wiring requirements over the conventional global referencing strategy. This is because the "local" reference electrodes are nearby in the tree architecture. This lowering of wiring requirements can help with reducing inter-wire coupling, reducing shielding requirements, reducing requirements on amplifier's gain and noise (thus also lowering amplifier energy), and also directly reduce the cost and weight.

To compare this invention with the direct global referencing strategy, the savings are in energy and area because of savings in ADC bit resolution. The required ADC resolution for the hierarchical topology can be calculated by $$\frac{1}{2} \log \frac{2\sigma^2 (1-\rho)}{q_e^2},$$

where $\sigma^2$ is the variance of the signal being sensed, $q_e^2$ is the ADC quantization noise, and p is the correlation between the two signals (where p>0.5, due to sensor spacing and location).

A specific embodiment of the invention was modeled and analyzed for ultra high density EEG sensing, using up to 9331 electrodes, much greater than conventional systems with up to 512 electrodes. As a byproduct of being able to reduce the ADC bit resolution of this system, energy savings of greater than a factor of 2.7 were achieved. The hierarchical technique goes a step further, and instead of viewing the decay of high spatial frequencies simply as a detriment to signal quality, it exploits it reducing energy and area requirements, enabling the user to dig deeper into the resolution of each sensor, as well as enabling higher sensor density.

Although the invention is illustrated and described herein with reference to specific embodiments, the invention is not intended to be limiting to the details shown. Rather, various modifications may be made in the details without departing from the invention.

Figure 5:
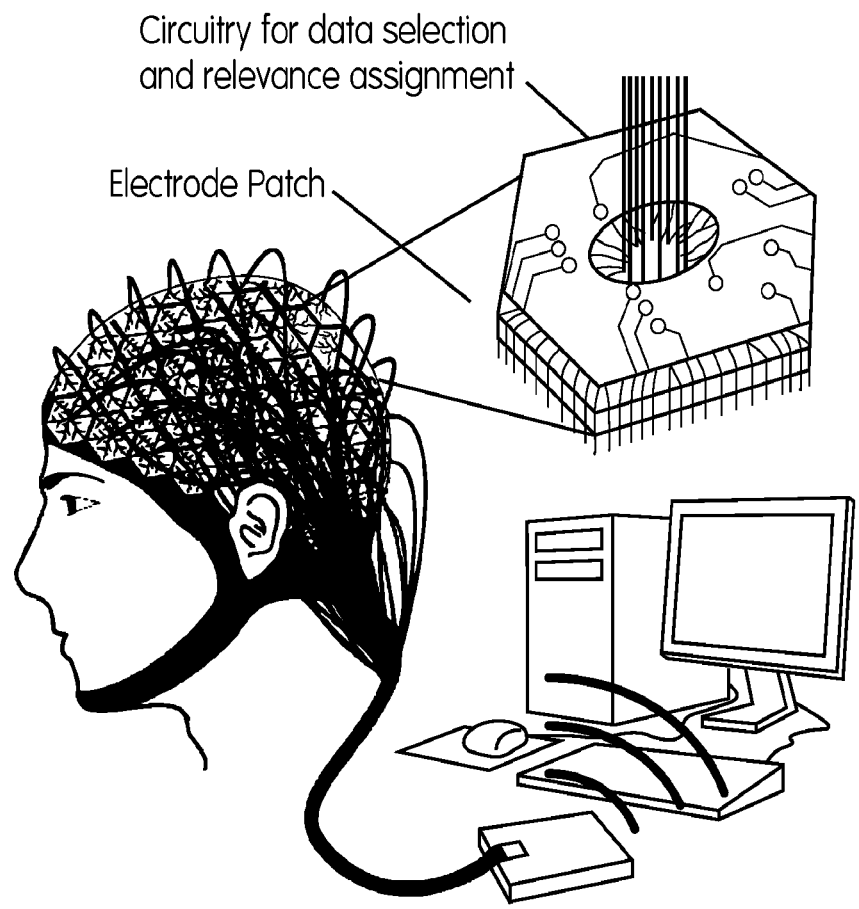
FIG. 5 shows an example of the use of the device on a human head, forming a neural web
Figure 6:
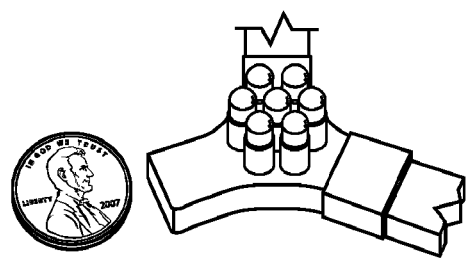
FIG. 6 shows a physical embodiment of a single set of probes held in place by a customized holder.

FIGS. 5 and 6 show various ways in which the electrodes can be held in place to ensure that they are spatially correlated when in use. Preferably, the electrodes will be embedded in a flexible material or medium that can be worn or placed on the body part where the biopotentials are being measured. FIG. 5 shows such an arrangement wherein the electrodes are held in place in the material of a cap that is worn on the head of the subject. FIG. 6 shows a plurality of the electrodes held in place by a bracket.

It should also be noted that the invention, to be operational, requires circuitry to read the biopotential differences and to store the differences in digital form for later analysis.

We claim:

1. A system for measuring biopotentials, comprising:
   a plurality of electrodes, arranged on a surface in a multi-level, hierarchal tree structure with respect to a global reference electrode;
   a plurality of analog to digital converters to perform a level-dependent analog-to-digital conversion of a difference in potentials, between each electrode and its parent electrode, the number of bits used in the conversion being dependent on the number of levels between each electrode and the global reference electrode.

2. The system of claim 1 further comprising a plurality of differential amplifiers, one for each electrode and its parent electrode, the differential amplifiers taking as inputs the biopotentials measured at each electrode and its parent electrode and outputting the difference in biopotentials between the electrodes.

3. The system of claim 2 further comprising a means for storing the differences in biopotentials for each electrode and its parent electrode.

4. The system of claim 1 wherein each electrode at a particular level in the tree structure can serve as a parent to one or more nodes at the next highest level in the tree structure.

5. The system of claim 1 wherein the electrodes are held in spatial relationships with respect to each other by a medium.

6. The system of claim 5 wherein the medium can be worn on the body of a subject.

7. The system of claim 1, the number of bits used in the digital conversion being the highest at the global reference electrode and reducing for each electrode based on the location of the electrode in the tree structure, with electrodes farther from the global reference node using fewer bits and electrodes nearer the global reference node using more bits.

8. A method for measuring biopotentials, comprising:
   arranging a plurality of electrodes in a multi-level, hierarchical tree structure with respect to a global reference electrode as the root of said tree, such that each electrode has exactly one parent electrode in the tree structure;
   measuring the difference in potential between each electrode and its parent electrode;
   converting each difference in potential to a digital value, the number of bits used in the conversion being dependent on the number of levels in the tree structure between each electrode and the global reference electrode.

9. The method of claim 8 wherein each electrode has as its parent the physically closest electrode which is in the next higher level of the tree structure.

10. The method of claim 8 further comprising of taking the sum of the differences in potential between an electrode and each parent in the path between the electrode and the global reference electrode to obtain the difference in potential between the electrode and the global reference electrode.

11. The method of claim 8, the number of bits used in the digital conversion being the highest at the global reference electrode and reducing for each electrode based on the location of the electrode in the tree structure, with electrodes farther from the global reference node using fewer bits and electrodes nearer the global reference node using more bits.

* * * * *

UNITED STATES PATENT AND TRADEMARK OFFICE
CERTIFICATE OF CORRECTION

PATENT NO. : 10,682,068 B2
APPLICATION NO. : 15/580249
DATED : June 16, 2020
INVENTOR(S) : Grover et al.

Page 1 of 1

It is certified that error appears in the above-identified patent and that said Letters Patent is hereby corrected as shown below:

In the Claims

Column 6, Line 27, Claim 10; Please replace "further comprising of taking" with --further comprising taking--

Signed and Sealed this
Tenth Day of November, 2020

Andrei Iancu
*Director of the United States Patent and Trademark Office*